United States Patent
Schmidt et al.

(10) Patent No.: US 12,290,702 B2
(45) Date of Patent: May 6, 2025

(54) WET PREPARATION OF RADIOTHERAPY SOURCES

(71) Applicant: ALPHA TAU MEDICAL LTD., Tel Aviv (IL)

(72) Inventors: Michael Schmidt, Kfar Saba (IL); Itzhak Kelson, Tel Aviv (IL)

(73) Assignee: Alpha Tau Medical Ltd, Jerusalem (IL)

( * ) Notice: Subject to any disclaimer, the term of this patent is extended or adjusted under 35 U.S.C. 154(b) by 773 days.

(21) Appl. No.: 17/092,269

(22) Filed: Nov. 8, 2020

(65) Prior Publication Data

US 2021/0128945 A1 May 6, 2021

Related U.S. Application Data

(63) Continuation of application No. PCT/IB2020/059317, filed on Oct. 5, 2020.

(60) Provisional application No. 62/913,184, filed on Oct. 10, 2019.

(51) Int. Cl.
*A61N 5/10* (2006.01)
*A61K 51/02* (2006.01)
*A61K 51/12* (2006.01)
*G21G 4/10* (2006.01)

(52) U.S. Cl.
CPC .......... *A61N 5/1014* (2013.01); *A61K 51/025* (2013.01); *A61K 51/1282* (2013.01); *G21G 4/10* (2013.01); *A61N 2005/1024* (2013.01); *A61N 2005/1085* (2013.01)

(58) Field of Classification Search
None
See application file for complete search history.

(56) References Cited

U.S. PATENT DOCUMENTS

| | | | |
|---|---|---|---|
| 5,322,644 A | 6/1994 | Dunn et al. | |
| 6,498,341 B2 | 12/2002 | Dehnert et al. | |
| 6,858,147 B2 | 2/2005 | Dukhin et al. | |
| 8,834,837 B2 | 9/2014 | Kelson et al. | |
| 9,908,788 B1 | 3/2018 | Litz et al. | |
| 2003/0092957 A1 | 5/2003 | Scott et al. | |
| 2003/0194364 A1* | 10/2003 | Bond | G21G 1/0005 423/2 |
| 2005/0079132 A1 | 4/2005 | Wang et al. | |
| 2006/0219956 A1* | 10/2006 | Bergman | G21G 4/08 250/493.1 |
| 2009/0275793 A1* | 11/2009 | Black | G21G 4/08 600/8 |
| 2013/0134098 A1 | 5/2013 | Kostedt, IV et al. | |
| 2015/0292061 A1 | 10/2015 | Fassbender et al. | |
| 2017/0267556 A1 | 9/2017 | Vidic | |
| 2018/0207105 A1 | 7/2018 | Fellows | |

FOREIGN PATENT DOCUMENTS

| | | |
|---|---|---|
| CA | 2374861 A1 | 6/2003 |
| JP | 2003185791 A | 7/2003 |
| JP | 2018086602 A | 6/2018 |
| KR | 20090011147 A | 2/2009 |
| RU | 2215798 C1 | 11/2003 |
| RU | 2317607 C1 | 2/2008 |
| RU | 2441842 C1 | 2/2012 |
| RU | 2513206 C1 | 4/2014 |
| RU | 2612543 C2 | 3/2017 |
| WO | 0029501 A1 | 5/2000 |
| WO | 2005051454 A1 | 6/2005 |
| WO | 2009134431 A1 | 11/2009 |
| WO | 2019183724 A1 | 10/2019 |
| WO | 2020099769 A1 | 5/2020 |

OTHER PUBLICATIONS

Larionov et al. Removal of natural radionuclides from underground water sources. Vodosnabzhenie i Sanitarnaya Tekhnika, (2), 10-19 (Year: 2015).*
Pavia et al. Timescales of hydrothermal scavenging in the South Pacific Ocean from 234th, 230th, and 228th. Earth and Planetary Science Letters, 506, 146-156 (Year: 2019).*
SG Application # 11202202423P Office Action dated Feb. 1, 2024.
AU Application # 2023203994 Office Action dated Apr. 15, 2024.
AU Application # 2023203996 Office Action dated Apr. 16, 2024.
AU Application # 2023203997 Office Action dated Apr. 20, 2024.
AU Application # 2020362983 Office Action dated Feb. 16, 2023.
Narbutt et al., "Gamma Emitting Radiotracers 224Ra, 212Pb and 212Bi from Natural Thorium," Applied Radiation and Isotopes, Elsevier Science Ltd., vol. 49, Nos. 1-2, pp. 89-91, year 1998.
El-Didamony et al., "Treatment of Phosphogypsum Waste Produced from Phosphate Ore Processing," Journal of Hazardous Materials, Elsevier B.V., vol. 244-245, pp. 596-602, year 2013.
Lauria et al., "A Sequential Analytical Method for the Determination of U-238, Th-232, Th-230, Th-228, Ra-228 and Ra-226 in Environmental Samples," The Science of the Total Environment, vol. 70, pp. 83-99, year 1988.
EP Application # 20875424.2 Search Report dated Oct. 23, 2023.
RU Applicaton # 2022103816 Office Action dated Nov. 3, 2023.
Afifi et al., "Extraction and Determination of Thorium and its Application on Geologic Samples using Trioctyl Phosphine Oxide," Arab Journal of Nuclear Science and Applications, vol. 45, issue 3, pp. 1-16, year 2012.

(Continued)

*Primary Examiner* — Tanisha Diggs
(74) *Attorney, Agent, or Firm* — Meitar Patents Ltd.; Daniel Kligler

(57) ABSTRACT

A method of accumulating radium radionuclides, comprising providing a first solution including thorium radionuclides and a thorium-binding extractant, wherein the first solution does not bind to radium, allowing a portion of the thorium radionuclides in the first solution to decay into radium atoms and collecting radium atoms resulting from the decay. The collected radium atoms may be included in a solution in which brachytherapy sources are dipped, in a manner which collects the radium atoms onto the source.

19 Claims, 5 Drawing Sheets

(56) References Cited

OTHER PUBLICATIONS

Khan et al., "Solvent Extraction of Thorium from Nitric Acid Solutions using DI-N-BUTYL Sulfoxide (DBSO) in Xylene", Journal of Radioanalytical and Nuclear Chemistry, Articles, vol. 198, No. 2, pp. 409-421, year 1995.
Swarzenski et al., "Is the Extraction of Thorium onto MnO2-coated Filter Cartridges Uniform?," USGS Open File Report, OFR 2004-1421, pp. 1-33, year 2004.
Reid et al., "Radium, Thorium, and Actinium Extraction from Seawater using an Improved Manganese-Oxide-Coated Fiber", Earth and Planetary Science Letters, issue 43, pp. 223-226, year 1979.
International Application # PCT/IB2020/059317 Search repor dated Jan. 11, 2021.
Kumar et al., "Utilization of Chemical Deposition Technique for Preparation of Miniature 170 Tm Sources and Preliminary Quality Assessment for Potential Use in Brachytherapy", Cancer Biotherapy and Radiopharmaceuticals, vol. 34, No. 1, pp. 24-32, Feb. 7, 2019.
Kuper et al., "Cytopathic effects of X-ray irradiation and MnO nanoparticles on human glioblastoma (U87)", Physics Procediam vol. 84, pp. 252-255, Dec. 12, 2016.
Avantor Inc., "MED1-4213, MED2-4213, MED3-4213", Technical Data Sheet, pp. 1-3, year 2018.
Solvay, "Specialty Polymers Eviva™ EV-500 Polysulfone", Technical Data Sheet, p. 1, year 1996-2021 downloaded from http://www.matweb.com/search/datasheet.aspx?matguid=b23cbb1f85034c27a7df0de0af845555.
RU Application # 2024103738 Office Action dated May 7, 2024.
JP Application # 2023177131 Office Action dated Aug. 27, 2024.

\* cited by examiner

WET PREPARATION OF RADIOTHERAPY SOURCES

FIELD OF THE INVENTION

The present invention relates generally to radiotherapy and particularly to methods of preparing alpha radiotherapy sources.

BACKGROUND OF THE INVENTION

Alpha particles are a powerful means for radiotherapy of certain types of tumors, including malignant tumors. One type of alpha radiotherapy sources are diffusing alpha-emitter radiation therapy (DART) sources loaded with radium-223 or radium-224 atoms, which have a half-life which is suitable (e.g., not too long and not too short) for therapeutic purposes.

U.S. Pat. No. 8,834,837 to Kelson describes a method for preparation of an alpha DART source, by positioning the source in a flux of radium-224 coming from a surface source of thorium-228.

US patent publication 2015/0292061 describes separation of radionuclide fission products from a proton-irradiated thorium target.

SUMMARY OF THE INVENTION

There is provided in accordance with embodiments of the present invention, a method of accumulating radium radionuclides, including providing a first solution including thorium radionuclides and a thorium-binding extractant, wherein the first solution does not bind to radium, allowing a portion of the thorium radionuclides in the first solution to decay into radium atoms; and collecting radium atoms resulting from the decay.

Optionally, the thorium-binding extractant comprises TOPO (tri-octyl phosphine Oxide). Optionally, collecting the radium atoms comprises collecting the radium atoms into a second solution. Alternatively or additionally, collecting the radium atoms comprises collecting the radium atoms onto a brachytherapy source. Optionally, collecting the radium atoms comprises collecting the radium atoms into a second solution and dipping the brachytherapy source into the second solution. Optionally, providing the first solution comprises introducing the first solution into a chamber with a second solution, such that the decay radium atoms diffuse into the second solution. Optionally, providing the first solution comprises providing a solution including a diluent having a low level of solubility with the second solution.

Optionally, the diluent has a specific weight lower than the specific weight of water. Optionally, the diluent comprises cyclohexane. Optionally, the second solution comprises a salt solution. Optionally, allowing a portion of the thorium radionuclides to decay into radium atoms comprises leaving the separation solution in a chamber with walls from a material which attracts radium for a decay period, and collecting the radium atoms comprises washing the radium atoms off the walls using a salt solution. Optionally, allowing a portion of the thorium radionuclides in the separation solution to decay into radium atoms comprises placing the first solution in a chamber from which radium atoms are detachable without using an acid of pH lower than 4.

In some embodiments, providing the first solution comprises providing a separation solution of a diluent having a low level of solubility and a thorium-binding extractant, combining the prepared separation solution with an initial solution including thorium radionuclides, so that thorium radionuclides from the initial solution bind to the thorium-binding extractant and separating the separation solution from the initial solution, to form the first solution.

There is further provided in accordance with embodiments of the present invention, a method of producing a brachytherapy source, comprising generating a solution including radium atoms; and dipping a brachytherapy source into the solution, in a manner which collects the radium atoms onto the source. Optionally, the method further includes coating the source with a protective coating which prevents the radium atoms from detaching from the source, but allows daughter nuclei of the radium atoms to leave the source upon decay of the radium atoms.

Optionally, coating the source with a protective coating comprises coating by polysulfone or Polydimethylsiloxane. Optionally, coating the source with a protective coating comprises coating by alumina. Optionally, the method further includes coating the source with manganese oxide prior to dipping the source in the solution. Optionally, the method further includes heating the source and allowing it to slowly cool, after coating the source with manganese oxide. Optionally, the source comprises a manganese oxide source. Optionally, the solution comprises a salt solution or distilled water.

There is further provided in accordance with embodiments of the present invention, an apparatus for accumulating radium radionuclides, comprising a first vessel holding a first solution including thorium radionuclides and a thorium-binding extractant, a second vessel holding a second solution including radium atoms, a pump; and a processor configured to control the pump to introduce a third solution into the first vessel, and after a sufficient period in which radium atoms are collected, to remove the third solution from the first vessel and transfer it to the second vessel.

There is further provided in accordance with embodiments of the present invention, a brachytherapy source, comprising a base sized and shaped for insertion into a human organ for brachytherapy, a manganese oxide coating over the base; and radium atoms attached to the manganese oxide coating. Optionally, the base comprises a metal base.

Alternatively, the base comprises a non-metal base. Optionally, the brachytherapy source further includes a protective coating which prevents the radium atoms from detaching from the source, but allows daughter nuclei of the radium atoms to leave the source. Optionally, the protective coating allows daughter nuclei of the radium atoms to leave the source due to energy resulting from decay of the radium atoms. Alternatively or additionally, the protective coating allows daughter nuclei of the radium to leave the source due to diffusion. Optionally, the protective coating comprises polysulfone and/or alumina. Optionally, the brachytherapy source does not include more thorium atoms than 0.1% of the radium atoms on the source. Optionally, the radium atoms are attached to the manganese oxide coating in a manner resulting from annealing.

DETAILED DESCRIPTION OF EMBODIMENTS

An aspect of some embodiments of the invention relates to a method of generating a solution including radioactive radium atoms. The method includes providing a container including thorium atoms in a solution which attracts thorium but does not attract radium, and allowing the thorium to decay into radium. In some embodiments, the container further includes a second solution which does not mix with the thorium solution. The radium atoms are allowed to diffuse into the second solution, which is removed from the container with the radium atoms, when a sufficient amount of radium is collected. In other embodiments, the radium atoms are allowed to accumulate on walls of the container and are collected from the walls after the thorium solution is removed from the container. The thorium optionally includes thorium-228. It is noted, however, that the principles of the present invention may be used also with thorium-227 for example resulting from Actinium-227.

An aspect of some embodiments of the invention relates to a method of generating a radium brachytherapy source. The method includes dipping a brachytherapy source into a solution including radium atoms, in a manner which collects the radium atoms onto the source.

The radium solution is optionally generated using the above described method. Alternatively, the radium solution is generated using any other suitable method known in the art, such as by separating radium from thorium using a fractionating column.

Overview

Figure 1:
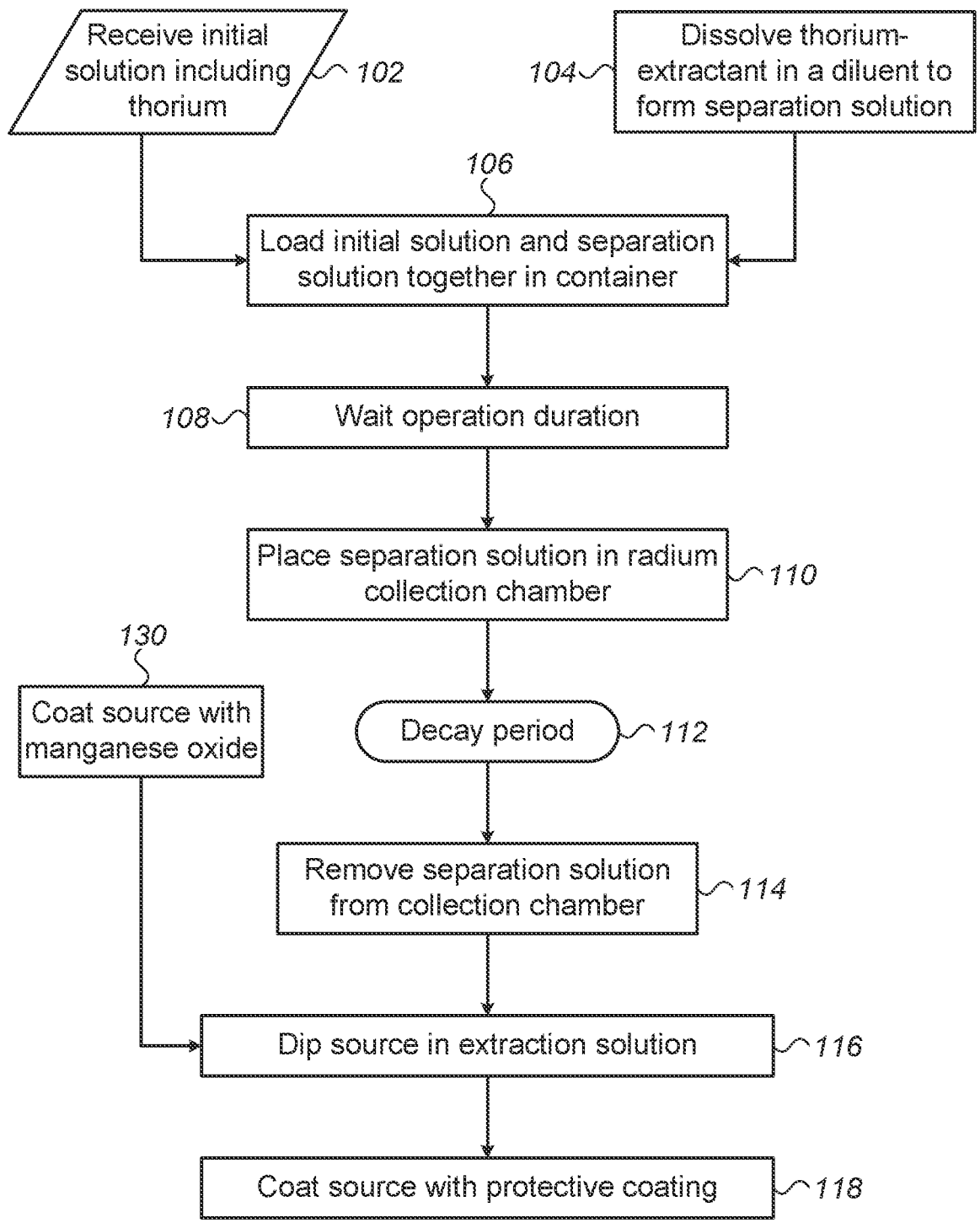
FIG. 1 is a flowchart of acts performed in producing an alpha DART brachytherapy source, in accordance with an embodiment of the invention.
Figure 2:
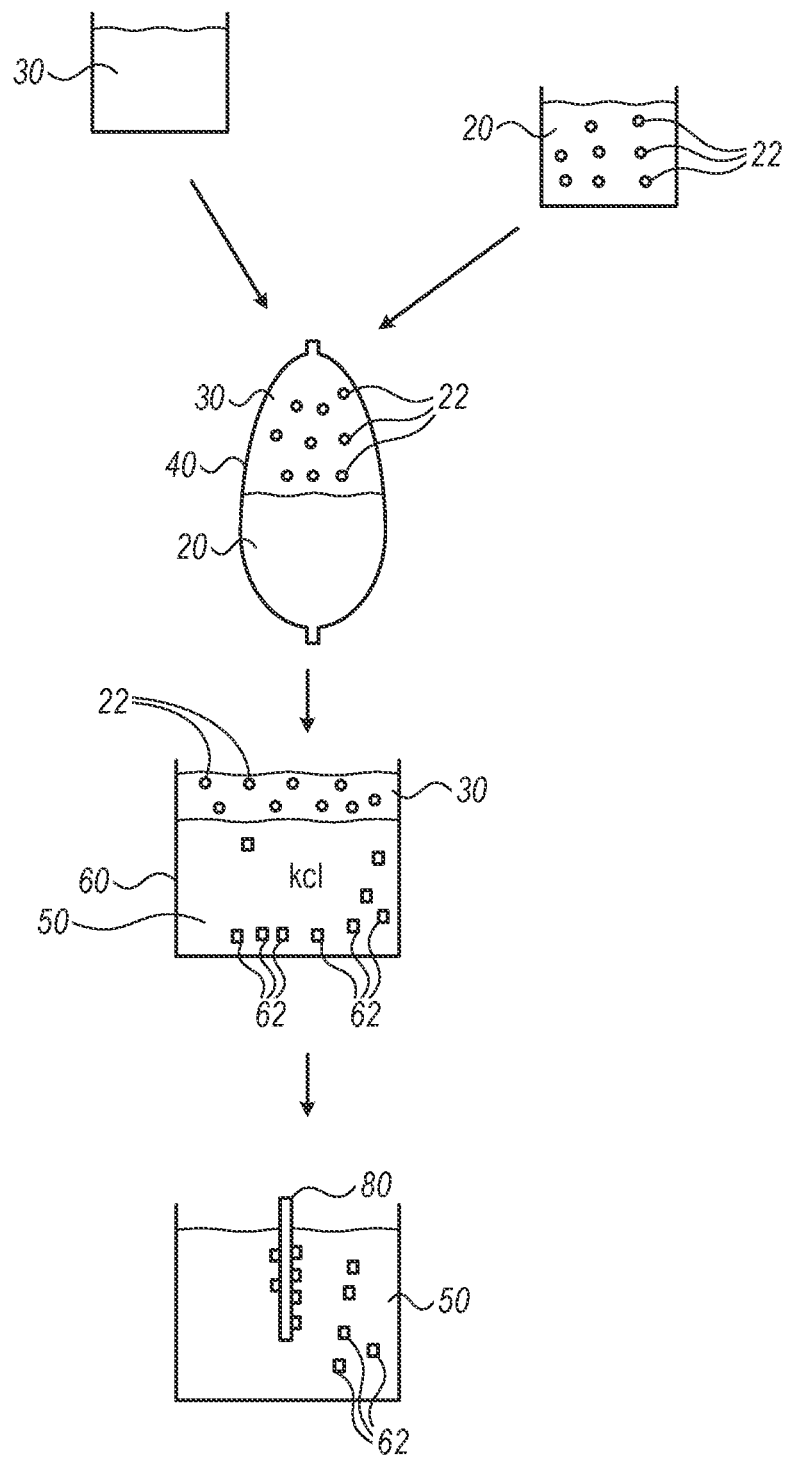
FIG. 2 is a schematic illustration of a process for producing a radium brachytherapy source, in accordance with an embodiment of the invention.

FIG. 1 is a flowchart of acts performed in producing a radium brachytherapy source, in accordance with an embodiment of the invention. FIG. 2 is a schematic illustration of the process of FIG. 1.

The process of FIG. 1 optionally begins with receiving (102) an initial solution 20 including thorium-228 radionuclides 22. A separation solution 30 formed of a thorium-binding extractant, which binds with thorium but does not bind with radium, dissolved in a diluent having a low level of solubility (i.e., less than 0.1%) in water and optionally a specific-weight different from that of water, such as cyclohexane, is prepared (104). Separation solution 30 is loaded (106) into a container 40 including the received (102) initial solution 20. After an operation duration (108), the thorium radionuclides 22 from the initial solution 20 attach to the thorium-binding extractant in the separation solution 30. It is noted that the diluent prevents the separation solution 30 from mixing with the initial solution 20.

Separation solution 30, which now includes thorium radionuclides 22 is separated from initial solution 20, and is placed (110) in a radium collection chamber 60, in which it is left for a decay period (112), of a length of time sufficient for a percentage of the thorium radionuclides to undergo a radioactive decay into radium. After the decay period (112), separation solution 30 is removed (114) from radium collection chamber 60, leaving the radium atoms 62, which do not bind to separation solution 30, within radium collection chamber 60. A liquid extraction solution 50 is used to wash the radium atoms 62 out of radium collection chamber 60. Then, a brachytherapy source 80 is dipped (116) in the extraction solution 50 and collects radium atoms 62 on its surface. Optionally, before being dipped (116) into the extraction solution 50, brachytherapy source 80 is coated (130) by a manganese oxide, suitable for attracting and/or binding the radium atoms 62 to the source 80.

In some embodiments, after brachytherapy source 80 is removed from extraction solution 50, the source is coated (118) by a suitable coating which prevents radium atoms 62 from leaving the source, while allowing daughter Radon nuclides to leave the source 80. Particularly, the coating is optionally sufficient to prevent release of radium atoms during heat sterilization. Alternatively, other methods of sterilization may be used, such as gamma ray sterilization, and in such cases the coating may be thinner or no coating is used at all.

In some embodiments, the coating comprises a polysulfone, for example MED2-4213 produced by Solvay. Alternatively or additionally, the coating comprises Polydimethylsiloxane (PDMS), for example Eviva EV-500 provided by Specialty Polymers, or Parylene N. The coating optionally has a thickness which allows diffusion of Radon through the coating. The coating optionally has a thickness of less than 10 microns, less than 5 microns, less than 1 micron, less than 0.5 microns or even less than 0.3 microns. In some embodiments, the coating has a thickness of at least 0.05 microns or even at least 0.1 microns. In other embodiments, for example when the coating comprises a PDMS coating, the coating is relatively thick and has a thickness of at least 1 micron, at least 3 microns or even at least 5 microns or at least 8 microns.

In some embodiments, the coating comprises aluminum-oxide, also known as alumina. The alumina coating is optionally sufficiently thin to allow exit of radon due to radioactive recoil. The alumina coating is optionally generated using atomic layer deposition (ALD), and has a thickness of less than 50 nanometers, less than 10 nanometers or even less than 6 nanometers.

In some embodiments, before coating (118) brachytherapy source 80, the brachytherapy source 80 is annealed by heating and allowing it to slowly cool. Optionally, in annealing, the brachytherapy source 80 is heated to at least 275° Celsius, to at least 350° Celsius or even to at least 400° Celsius. In some embodiments, the annealing is performed in a low oxygen environment, such as in vacuum, or in an inert gas environment.

Separation Solution Details

Acidic solution 20 including thorium-228 is commercially available from various providers, including, for example, Eckert-Ziegler in Germany and Oak ridge national laboratory (ORNL) in the United States.

The preparation (104) of separation solution 30 is performed using any suitable method known in the art, such as any of the methods described in Afifi et al, "Extraction and Determination of Thorium and its application on Geologic Samples using Trioctyl Phosphine Oxide", Arab Journal of Nuclear Science and Applications, 45(3), 2012, the disclosure of which is incorporated herein by reference.

In some embodiments, the thorium-binding extractant comprises an organic extractant, such as TOPO (tri-octyl phosphine Oxide), tributyl phosphate, N,N,N',N'-terahexylsuccinyl-amide, N-alkyl amides, trialkyl-methylammonium nitrate, didodecylphosphoric acid, 2-ethylhexyl phenyl-phosphoric acid, diisobutyl ketone or hexa acetate calixarene.

Alternatively or additionally, the thorium-binding extractant comprises one or more sulfoxides, such as dibutyl-n-sulfoxide (DBSO), as described, for example, in Khan et al., "Solvent Extraction of Thorium From Nitric Acid Solutions Using Di-N-Butyl Sulfoxide (Dbso) in Xylene", Journal of Radioanalytical and Nuclear Chemistry, December 1995, col. 198, issue 2, pp. 409-421, the disclosure of which is incorporated herein by reference.

In some embodiments, the thorium-binding extractant comprises an extractant which binds to lead, in addition to binding to thorium, in order to reduce the amount of lead which enters extraction solution 50 and ultimately reaches source 80. Alternatively or additionally, a separate lead binding material is added to separation solution 30.

Alternatively to using cyclohexane as the diluent, other diluents are used, such as benzene, carbon tetra-chloride, chloroform, kerosene, toluene, dodecane or o-xylene.

In some embodiments, during the operation duration (108), container 40 is shaken to induce binding of the thorium to the thorium-binding extractant. In these embodiments, the operation duration (108) is at least 30 seconds, at least 1 minute, at least 3 minutes or even at least 5 minutes. The operation duration (108) is optionally less than 15 minutes, less than 10 minutes or even less than 5 minutes.

Alternatively, container 40 is not shaken during the operation duration (108). In accordance with this alternative, the operation duration is sufficiently long to allow diffusion of the thorium to the thorium-binding extractant, and is optionally at least 6 hours, at least 12 hours or even at least 24 hours.

Container 40 is shown as being closed, which is useful particularly when it is shaken to induce binding. It is noted, however, that containers of other forms may be used, including open containers.

Radium Collection Details

In some embodiments, during decay period (112), extraction solution 50 is included with separation solution 30 and the thorium radionuclides 22 therein in radium collection chamber 60, such that the radium atoms 62 formed from decay of the thorium radionuclides 22 diffuse into extraction solution 50. Optionally, extraction solution 50 comprises distilled water. The distilled water optionally forms at least 80%, at least 90%, at least 95% or even at least 99% of the extraction solution 50. The use of distilled water was found to more easily transfer the radium atoms to brachytherapy source 80, than other solutions, such as salt solutions. Optionally, in embodiments in which extraction solution 50 comprises distilled water, radium collection chamber 60 is formed of a material to which radium does not tend to combine, such as Teflon. Alternatively, extraction solution 50 comprises a salt solution, such as potassium chloride (KCl). Salt solutions generally reduce the settling of radium on the walls of radium collection chamber 60, and thus can be used in embodiments in which radium collection chamber 60 comprises a glass container. It is noted, however, that extraction solution 50 may include a salt solution even in embodiments in which radium collection chamber 60 is not made of glass, but rather is made of other materials such as Teflon. Optionally, radium collection chamber 60 does not include interior walls or other elements which strongly bind to radium atoms 62 in a manner requiring an acid of pH of 4 or lower to extract the radium atoms 62 from the chamber. Thus, the radium atoms 62 may be collected in a non-acidic solution, which may be more convenient for transferring the radium atoms 62 to the brachytherapy source 80.

The salt in the salt solution 50 optionally has a concentration of at least 0.001 Mol or even at least 0.01 Mol. In some embodiments, the concentration of the salt in the salt solution is less than 0.1 Mol. Optionally, the salt solution has a pH of about 5 (±10%). Alternatively to a salt solution, extraction solution 50 comprises a weak acid having a pH of between 2-3. In accordance with this alternative, after removal (114) of separation solution 30 and before dipping (116) brachytherapy source 80 in extraction solution 50, extraction solution 50 is optionally titrated so as to be better suited for passing radium atoms 62 to brachytherapy source 80.

In some embodiments, instead of removing (114) separation solution 30 from radium collection chamber 60, extraction solution 50 is removed to a different container while separation solution 30 is left in radium collection chamber 60.

In other embodiments, during decay period (112), separation solution 30 and the thorium radionuclides 22 therein are located in radium collection chamber 60 on their own, and the radium atoms 62 formed by the decay settle on the walls of radium collection chamber 60. After decay period (112), separation solution 30 is removed from radium collection chamber 60 and extraction solution 50 is passed through radium collection chamber 60 to collect radium atoms 62 from the walls of the chamber. In these embodiments, extraction solution 50 optionally comprises a salt solution, such as potassium chloride (KCl), or a weak acid, suitable for washing the radium atoms 62 from the walls of radium collection chamber 60. Optionally, in these embodiments, radium collection chamber 60 is configured in a shape having a large surface area, for example a shape of a long and narrow column. For example, radium collection chamber 60 may have a shape of a long and narrow tube, having a diameter of less than 15 millimeters, less than 10 millimeters or even less than 5 millimeters. The length of the tube serving as radium collection chamber 60, is optionally chosen according to the amount of separation solution 30 used. In some embodiments, the tube has a length of at least 10 centimeters or even at least 15 centimeters. Optionally, in these embodiments, the tube has two openings, which allow flowing of extraction solution 50 through the tube from a first opening on one end to a second opening on the other end, in a manner washing the settled radium atoms 62 off the walls of the tube serving as radium collection chamber 60.

Alternatively to using extraction solution 50, separation solution 30 is left on its own for the sufficient time (112) for a percentage of the radionuclides to undergo a radioactive decay into radium. Source 80 is then dipped into separation solution 30 to collect radium atoms (62) on its surface. This alternative may be used especially in cases in which collection of some thorium radionuclides 22 on source 80 is acceptable, and there is no need to remove the thorium radionuclides 22 from the container in which source 80 is dipped. Optionally, in these embodiments, the container holding separation solution 30 comprises a material, such as Teflon, which does not bind the radium atoms 62.

Source Details

Brachytherapy source 80 may have substantially any shape suitable for brachytherapy treatment. Brachytherapy source 80 may have, for example, a cylinder shape, a flat surface shape, or a ball shape. In some embodiments, brachytherapy source 80 comprises a material which attracts radium atoms 62 from extraction solution 50. For example, brachytherapy source 80 may comprise a metal source or may be coated by a metal. These embodiments are particularly useful when extraction solution 50 comprises distilled water, which allows the radium atoms 62 to diffuse to a metal source. It is noted that in accordance with some of these embodiments, coating (130) brachytherapy source 80 by manganese oxide, is not necessary and may be skipped.

In some embodiments, brachytherapy source 80 comprises a material which does not interfere with one or more medical imaging modalities, such as ultrasound or MRI, to be used in implanting the brachytherapy source 80.

Alternatively or additionally, brachytherapy source 80 comprises a material for binding with a manganese oxide, which in turn binds to radium atoms 62. Optionally, brachytherapy source 80 comprises a metal base which is suitable for receiving the manganese oxide coating. Alternatively, brachytherapy source 80 comprises a non-metal base, which is metal coated by a metal that binds sufficiently to the manganese oxide coating. Alternatively, brachytherapy source 80 comprises any other material which can bind to a manganese oxide coating.

The manganese oxide optionally includes manganese dioxide ($MnO_2$). Alternatively, the manganese oxide comprises any other manganese oxide which binds radium, such as manganese (IV) dioxide, manganese (II) oxide (MnO), manganese (II,III) oxide ($Mn_3O_4$), manganese (III) oxide ($Mn_2O_3$) and manganese (VII) oxide ($Mn_2O_7$) or a mixture of various manganese oxides.

The coating (130) of brachytherapy source 80 by manganese oxide is optionally performed by dipping brachytherapy source 80 in potassium permanganate ($KMnO_4$). The coating (130) is optionally performed at a temperature of at least 60° Celsius, or even at least 80° Celsius, for example at about 90° Celsius. After coating brachytherapy source 80, the source and manganese oxide coating are optionally slowly cooled over at least an hour, or even at least 6 hours. Applicant has found that the slow cooling achieves a more stable coating. Alternatively, any other suitable method for coating by manganese oxide, is used. In other embodiments, any other material suitable to bind radium atoms 62 is used instead of, or in addition to, manganese oxide.

In some embodiments, before dipping brachytherapy source 80 in extraction solution 50, extraction solution 50 is diluted, concentrated or undergoes chemical alteration. For example, as mentioned above, extraction solution 50 may be titrated to a desired pH level, e.g., about 5. The dilution and/or concentration are optionally performed to bring the radium concentration in extraction solution 50 within desired limits. Optionally, the radium concentration is at least 3 microcurie per milliliter, at least 5 microcurie per milliliter or even at least 10 microcurie per milliliter. In some embodiments, the radium concentration is lower than 60 microcurie per milliliter, lower than 50 microcurie per milliliter or even lower than 40 microcurie per milliliter.

The dipping (116) of brachytherapy source 80 in extraction solution 50 is optionally performed for at least an hour, at least 5 hours or even at least 10 hours. Alternatively, methods known in the art for expediting the collection of radium on brachytherapy source 80, such as shaking and/or mixing, are used. In some embodiments, the extraction solution 50 is heated in order to expedite the collection of radium on brachytherapy source 80. The extraction solution 50 is optionally heated to a temperature which generates currents in the solution, such as at least 50 Celsius, at least 60° Celsius, at least 75 Celsius or even at least 80° Celsius. Optionally the solution is heated to a temperature not greater the 90° Celsius or even not greater than 80° Celsius. In accordance with this alternative, the dipping is optionally performed for less than 3 hours, less than an hour or even less than 30 minutes. The time of dipping (116) of brachytherapy source 80 in extraction solution 50 is optionally selected according to a desired activity of the source and the concentration of radium in extraction solution 50.

In an embodiment for large scale production of brachytherapy sources 80, the rate of generation of radium atoms 62 in radium collection chamber 60 is monitored and when the rate is below a desired level, separation solution 30 is replaced with a different batch of separation solution 30 having a higher density of thorium. Alternatively, a concentrated separation solution 30 having a high density of thorium is added to the separation solution 30 currently in radium collection chamber 60. Optionally, before adding the concentrated separation solution 30 having a high density of thorium, a portion of the separation solution 30 having a low density of thorium is removed from radium collection chamber 60 to make room for the concentrated separation solution 30. It is noted that instead of monitoring the actual rate of thorium decay into radium, the rate is estimated based on the half-life of thorium and the original concentration of thorium in separation solution 30, and accordingly the time of addition and/or replacement of separation solution 30 is preselected.

The concentration of thorium in separation solution 30 when in radium collection chamber 60 is optionally at least 0.08 millicurie, at least 0.1 millicurie, or even at least 0.2 millicurie in each milliliter. Applicant has found that use of higher concentrations of thorium may damage cyclohexane, by causing release of hydrogen atoms, and therefore the concentration of thorium in separation solution 30 is optionally not greater than 2 millicurie or even not greater than 1 millicurie to each milliliter. In some embodiments, upper and lower limits are defined for the concentration of thorium in separation solution 30. When the concentration reaches the lower limit, separation solution 30 is replaced, or a highly concentrated thorium solution is added to radium collection chamber 60 to bring the thorium concentration to the upper limit.

The method of FIG. 1 does not depend on the quality (e.g., purity) of the initial solution 20, as the radium directed onto the brachytherapy source is separated from the initial solution 20 before the radium is directed to the brachytherapy source. Accordingly, the resulting brachytherapy source may be produced without thorium mixed with the radium, or at least with low amounts of thorium atoms, such as less than one percent of the number of radium atoms on the brachytherapy source, less than 0.1% of the radium atoms or even less than 0.01% of radium atoms on the brachytherapy source. It is noted, however, that in some cases a brachytherapy source including both radium and thorium is desired. In such cases, a desired percentage of thorium may be achieved by mixing a solution with a desired concentration of thorium into extraction solution 50.

The method of FIG. 1 also allows high utilization of the thorium.

Optionally, the method of FIG. 1 does not require high temperatures and in some embodiments, the entire process of FIG. 1 is carried out at temperatures lower than 180° Celsius or even lower than 140° Celsius. In other embodiments, however, one or more stages of the method may require high temperatures higher than 250° Celsius, or even higher than 300° Celsius or 350° Celsius.

Chambers

Figure 3A:
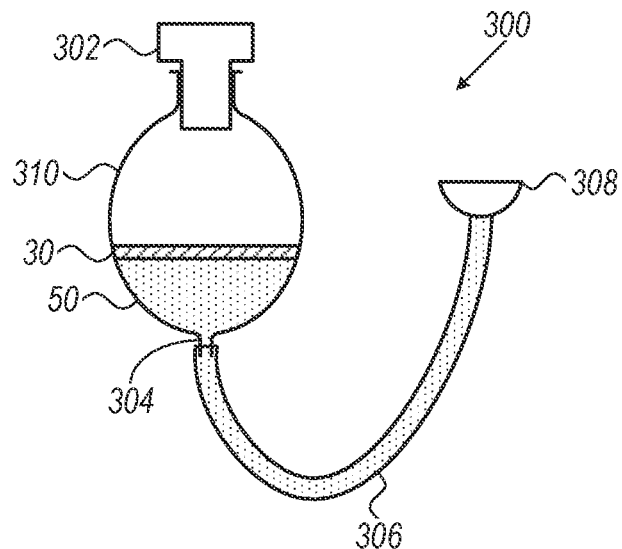
FIGS. 3A-3B show a chamber system before and after a radium decay period, in accordance with embodiments of the present invention.
Figure 3B:
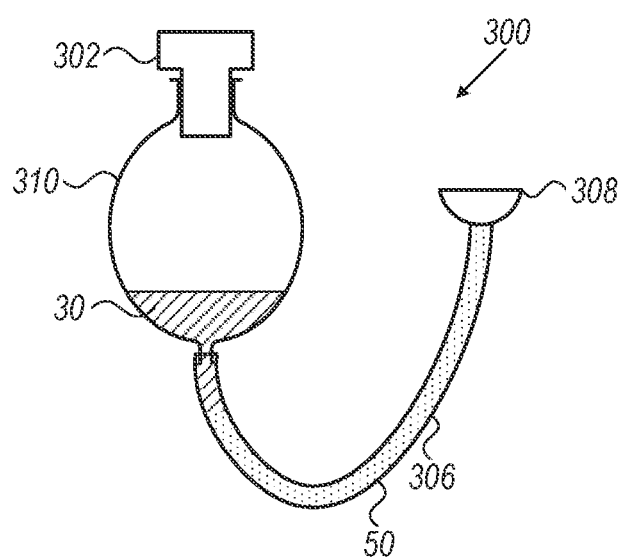

FIGS. 3A-3B show a chamber system 300 before and after decay period (112), in accordance with embodiments of the present invention. Chamber system 300 is a possible implementation of chamber 60 discussed above. A chamber 310 of system 300 comprises an upper cork 302 for loading separation solution 30 with thorium radionuclides 22 therein into the chamber 310. On a bottom side, chamber 310 comprises a narrow opening 304, which connects to a narrow Teflon tube 306, with a distal septum 308 through which extraction solution 50 is introduced into chamber 310. Septum 308, optionally made of a silicone or rubber, allows introduction and removal of liquids by a needle, without leakage.

Placing (110) separation solution 30 in chamber 310 is performed through an upper opening of chamber 310, which is sealed by upper cork 302. Before, after and/or concurrently with the placing of separation solution 30, extraction solution 50 of a suitable amount is introduced into chamber 310 through septum 308. Extraction solution 50 fills narrow Teflon tube 306 and a portion of chamber 310. Because separation solution 30 is lighter than extraction solution 50, separation solution 30 floats on extraction solution 50, as shown in FIG. 3A. After decay period (112), extraction solution 50 is removed from chamber 310 through septum 308, so that only separation solution 30 remains in chamber 310, as shown in FIG. 3B. It is noted that a small portion of extraction solution 50 optionally remains in narrow Teflon tube 306, such that not all of extraction solution 50 is extracted from chamber system 300. This is advantageous in order to make sure that no meaningful portion of separation solution 30, which could contaminate extraction solution 50, leaves chamber system 300, with extraction solution 50. The size of narrow Teflon tube 306 is optionally selected to minimize, on the one hand, the amount of extraction solution 50 remaining in chamber system 300, while, on the other hand, preventing remnants of separation solution 30 from leaving chamber system 300 with extraction solution 50. It is noted that instead of Teflon tube 306, a tube of any other suitable material may be used, such as silicon or rubber. This option is particularly useful in cases in which separation solution 30 does not enter the tube, and hence there is no problem of incompatibility between separation solution 30 and the material forming the tube.

Thereafter, an additional extraction solution 50 may be introduced into chamber 310, through septum 308, to collect radium atoms from the same separation solution 30. When the concentration of thorium in separation solution 30 goes below a threshold, an additional amount of separation solution 30 with a high concentration of thorium is introduced into chamber 310, through cork 302. Thus, system 300 can be used for continuous production of extraction solutions 50 carrying radium.

In accordance with some embodiments, the placing (110) of separation solution 30 in chamber 310 is performed at a much lower rate than the introducing of extraction solution 50 into chamber 310. For example, the placing (110) of separation solution 30 in chamber 310 may be performed once every 10, every 100 or even every 1000 stages of introducing of extraction solution 50 into chamber 310. Thus, the placing (110) of separation solution 30 in chamber 310 may be viewed in these embodiments as an initialization stage.

Figure 4A:
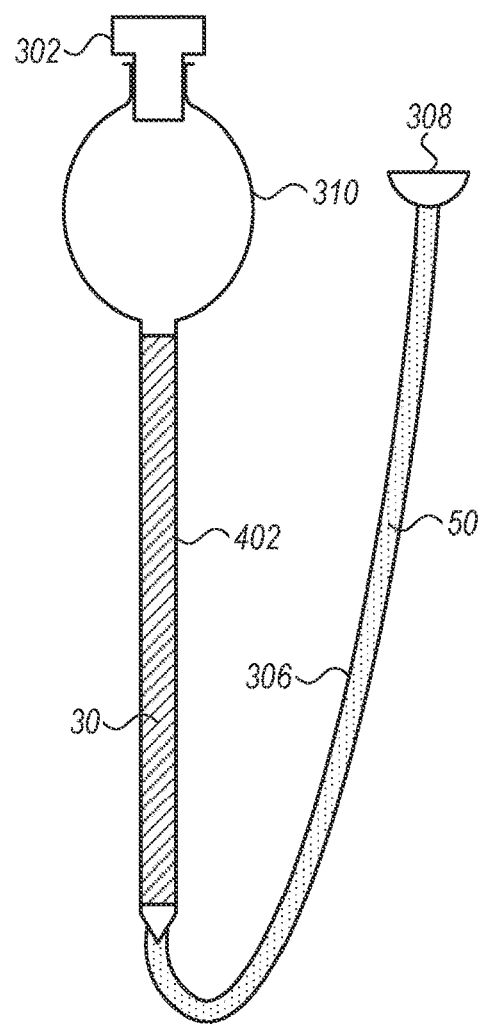
FIGS. 4A-4B show a chamber system before and after decay period, in accordance with other embodiments of the present invention.
Figure 4B:
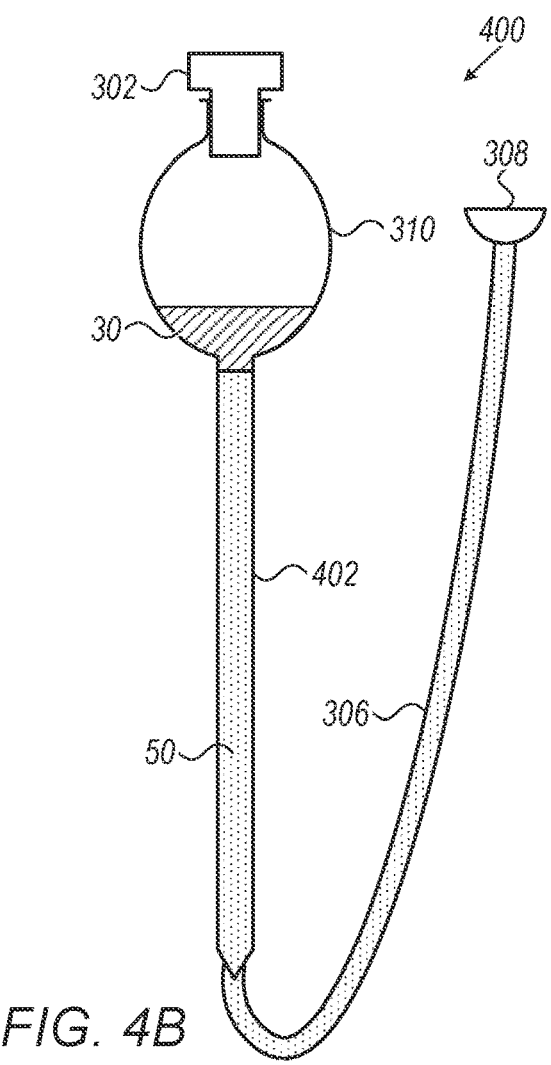

FIGS. 4A-4B show a chamber system 400 before and after decay period (112), in accordance with other embodiments of the present invention. In system 400, chamber 310 has a narrow extension 402 suitable for collecting radium atoms on its inner walls.

At a system initialization stage, separation solution 30 with thorium radionuclides therein, is loaded, generally through the opening sealed by upper cork 302, into narrow extension 402, as shown in FIG. 4A. After a first decay period (112), extraction solution 50 is loaded into narrow extension 402, through septum 308 and tube 306, pushing separation solution 30 into chamber 310, as shown in FIG. 4B. Extraction solution 50 collects radium atoms from the walls of narrow extension 402, and is removed through septum 308 along with the radium atoms. Separation solution 30 then returns back into narrow extension 402, as shown in FIG. 4A, and another round of radium atom production begins.

Figure 5:
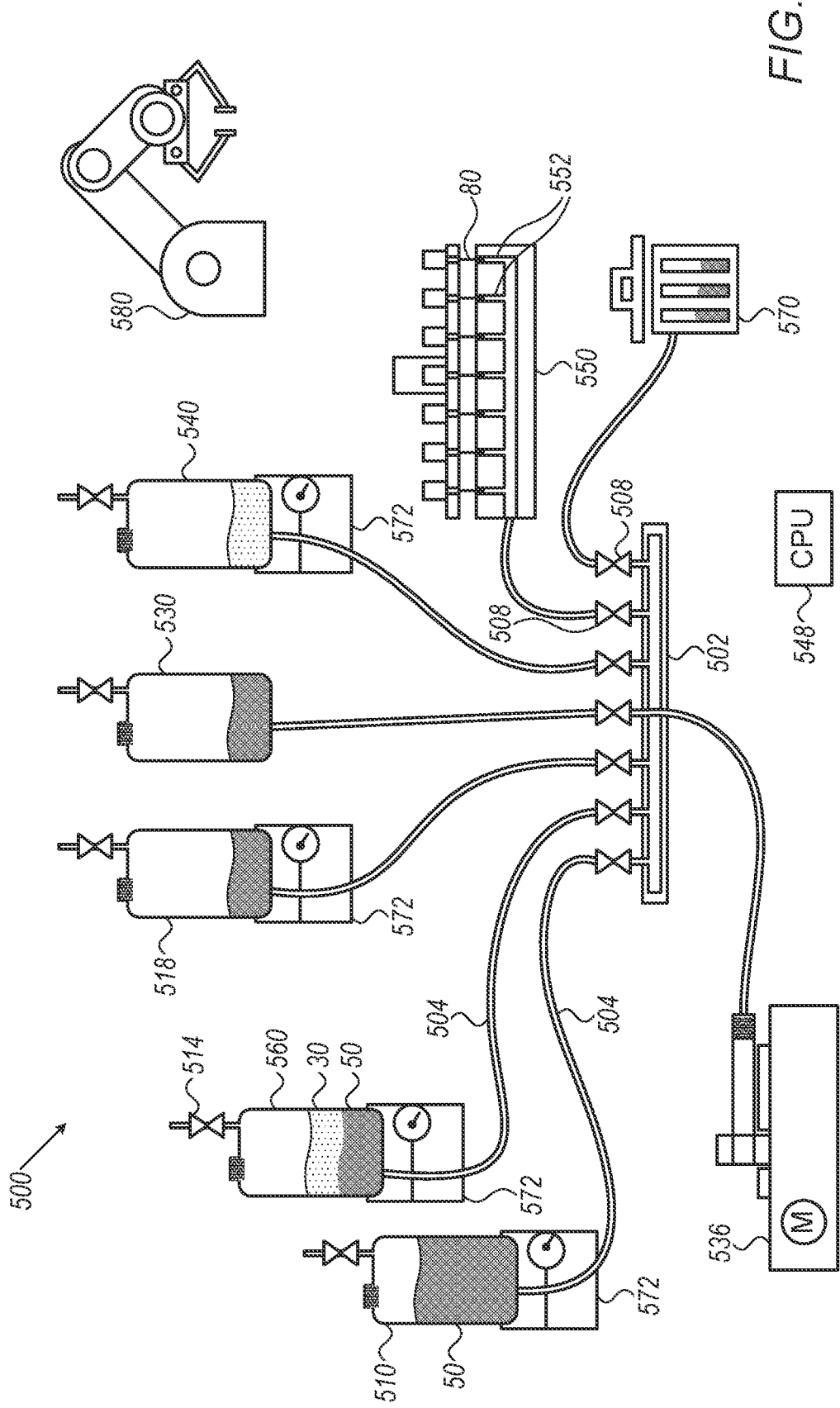
FIG. 5 is a schematic illustration of a system for producing alpha DART brachytherapy sources, in accordance with an embodiment of the invention.

FIG. 5 is a schematic illustration of a system 500 for producing alpha DART brachytherapy sources, in accordance with an embodiment of the invention. System 500 comprises a manifold 502 which connects through valves 508, and liquid tubes 504, to various containers. The containers include an extraction solution 50 vessel 510, a radium collection chamber 560 in which radium atoms 62 (FIG. 2) formed from decay of the thorium radionuclides 22 diffuse into extraction solution 50. The containers optionally further include an evaluation chamber 518, a radium storage vessel 530 and a water chamber 540. In some embodiments, manifold 502 is connected to one or more multi-compartment dipping vessels 550, which include a plurality of dipping compartments 552, arranged to receive elements to be converted into brachytherapy sources 80, by accumulating radium atoms. A robotic arm 580 is optionally used to insert brachytherapy sources 80 into dipping compartments 552 and remove them therefrom. A pump 536 is optionally connected to manifold 502 and used to transfer liquids between the containers of system 500. A dump 570 is optionally connected to one of valves 508 of manifold 502, to receive waste liquids not required anymore.

In some embodiments, one or more of the containers, such as extraction solution vessel 510, radium collection chamber 560, evaluation chamber 518 and/or water chamber 540 are placed on respective scales 572, which are used to monitor the amount of liquid in the containers. Alternatively or additionally, any other sensors for monitoring the content of the containers may be used.

A CPU 548 optionally controls the operation of system 500 by sending control commands to valves 508, pump 536 and/or robotic arm 580. The commands from CPU 548 are sent over wires or wirelessly using any suitable method known in the art. Valves 508 are generally kept closed, are opened when required to pass liquid through the specific valve and closed again after the liquid is transferred.

In operation, pump 536 transfers an amount of extraction solution 50 from vessel 510 to radium collection chamber 560. Before, in parallel and/or thereafter, a separation solution 30 is introduced into radium collection chamber 560 through an upper valve 514. After a predetermined time, and/or after determining that sufficient radium was collected, pump 536 retrieves extraction solution 50 from collection chamber 560 to evaluation chamber 518, where the extraction solution 50 and/or its radium content are evaluated. If the quality of the extraction solution 50 is sufficient, pump 536 transfers the extraction solution 50 to radium storage vessel 530. If, however, the concentration of extraction solution 50 requires adjustment, pump 536 transfers a required amount of water from water chamber 540 to evaluation chamber 518. Alternatively or additionally, extraction solution 50 is returned to collection chamber 560 to receive more radium. In parallel to the generation of the radium extraction solution 50, the radium extraction solution 50 is transferred to one or more multi-compartment dipping vessels 550 where brachytherapy sources 80 are dipped into the radium extraction solution 50. System 500 may include any number of collection chambers 560 connected to a single manifold 502, for parallel generation of the radium solution.

As shown, valves 508 are arranged linearly along manifold 502. In other embodiments, however, tubes 504 and/or valves 508 are arranged radially on manifold 502. Optionally, manifold 502 has a half or complete sphere shape. In order to transfer liquid between two containers, the valve 508 connecting to the source container is opened and pump 536 extracts an amount of liquid therefrom into an internal chamber of the pump. Then, the valve 508 connecting to the source container is closed, the valve connecting to the destination container is opened and the pump is operated to push the liquid in its internal chamber to the destination container.

CONCLUSION

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. It is particularly noted that although some of the dependent claims depend only on one parent claim, this is due to formal requirements of some jurisdictions, and unless unfeasible or specifically stated, the present invention is considered to include all combinations of dependent claims. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

The invention claimed is:

1. A method of accumulating radium radionuclides, comprising:
    providing a first solution including thorium radionuclides and a thorium-binding extractant, wherein the first solution does not bind to radium, such that radium atoms resulting from decay of the thorium diffuse out of the first solution;
    allowing a portion of the thorium radionuclides in the first solution to decay into radium atoms;
    allowing the radium atoms to diffuse out of the first solution; and
    collecting radium atoms resulting from the decay that diffused out of the first solution, from out of the first solution,
    wherein providing the first solution comprises introducing the first solution into a chamber with a second solution, which does not mix with the first solution, such that the decay radium atoms diffuse into the second solution, and
    wherein the first solution is lighter than the second solution.

2. The method of claim 1, wherein the thorium-binding extractant comprises TOPO (tri-octyl phosphine Oxide).

3. The method of claim 1, wherein collecting the radium atoms comprises collecting the radium atoms into a second solution.

4. The method of claim 1, wherein collecting the radium atoms comprises collecting the radium atoms onto a brachytherapy source.

5. The method of claim 4, wherein collecting the radium atoms comprises collecting the radium atoms into a second solution and dipping the brachytherapy source into the second solution.

6. The method of claim 1, wherein providing the first solution comprises providing a solution including a diluent having a low level of solubility with the second solution.

7. The method of claim 6, wherein the diluent has a specific weight lower than the specific weight of water.

8. The method of claim 6, wherein the diluent comprises cyclohexane.

9. The method of claim 1, wherein the second solution comprises a salt solution.

10. The method of claim 1, wherein allowing a portion of the thorium radionuclides to decay into radium atoms comprises leaving the first solution in a chamber with walls from a material which attracts radium for a decay period, and wherein collecting the radium atoms comprises washing the radium atoms off the walls using a salt solution.

11. The method of claim 1, wherein allowing a portion of the thorium radionuclides to decay into radium atoms comprises placing the first solution in a chamber from which radium atoms are detachable without using an acid of pH lower than 4.

12. The method of claim 1, wherein providing the first solution comprises:
    providing a separation solution of a diluent having a low level of solubility and a thorium-binding extractant;
    combining the prepared separation solution with an initial solution including thorium radionuclides, so that thorium radionuclides from the initial solution bind to the thorium-binding extractant; and
    separating the separation solution from the initial solution, to form the first solution.

13. The method of claim 4, and comprising coating the brachytherapy source with a protective coating which prevents the radium atoms from detaching from the source, but allows daughter nuclei of the radium atoms to leave the source upon decay of the radium atoms.

14. The method of claim 13, wherein coating the brachytherapy source with a protective coating comprises coating by polysulfone or Polydimethylsiloxane.

15. The method of claim 13, wherein coating the brachytherapy source with a protective coating comprises coating by alumina.

16. The method of claim 5, and comprising coating the brachytherapy source with manganese oxide prior to dipping the source into the second solution.

17. The method of claim 16, and comprising heating the brachytherapy source and allowing it to slowly cool, after coating the brachytherapy source with manganese oxide.

18. The method of claim 5, wherein the brachytherapy source comprises a manganese oxide source.

19. The method of claim 1, wherein the thorium radionuclides remain in the first solution while the radium atoms diffuse out of the first solution.

* * * * *